(12) United States Patent
Farrar et al.

(10) Patent No.: US 7,988,961 B2
(45) Date of Patent: Aug. 2, 2011

(54) GUT COMMENSAL BACTERIUM AND METHODS OF USING THE SAME

(75) Inventors: Mark Farrar, Leeds (GB); Simon Carding, Leeds (GB)

(73) Assignee: Plant Bioscience Limited (GB)

( * ) Notice: Subject to any disclaimer, the term of this patent is extended or adjusted under 35 U.S.C. 154(b) by 0 days.

(21) Appl. No.: 11/814,739

(22) PCT Filed: Jan. 24, 2006

(86) PCT No.: PCT/GB2006/000222
§ 371 (c)(1),
(2), (4) Date: Jul. 25, 2007

(87) PCT Pub. No.: WO2006/079790
PCT Pub. Date: Aug. 3, 2006

(65) Prior Publication Data
US 2008/0131402 A1    Jun. 5, 2008

(30) Foreign Application Priority Data

Jan. 25, 2005   (GB) .................................. 0501540.9

(51) Int. Cl.
*A61K 35/74* (2006.01)
(52) U.S. Cl. ...... 424/93.4; 424/93; 435/252.1; 435/325; 435/69.1; 435/6; 435/320.1
(58) Field of Classification Search .................. None
See application file for complete search history.

(56) References Cited

FOREIGN PATENT DOCUMENTS

EP    0 965 641 A    12/1999

OTHER PUBLICATIONS

Whitehead, et al., *Heterologous expression of the Bacteroides ruminicola xylananse gene in Bacteroides fragilis and Bacteroides uniformis*, Jul. 21, 1989, pp. 61-65, vol. 66, Fems Microbiology Letters.
Steidler, et al., *Biological containment of genetically modified Lactococcus lactis for intestinal delivery of human interleukin* Jul. 10, 2003, pp. 785-789, vol. 21, Nature Biotechnology, Nature Publishing Group.
Steidler, et al., *Treatment of Murine Colitis by Lactococcus lactis Secreting Interleukin-10*, Aug. 25, 2000, pp. 1352-1355, vol. 289, Science, American Association for the Advancement of Science, US.
Selinger, et al., *The Rumen: A Unique Source of Enzymes for Enhancing Livestock Production*, Oct. 1996, pp. 263-284, vol. 2, No. 5, Anaerobe.
Farrar, et al., *Engineering of the gut commensal bacterium Bacteroides ovatus to produce and secrete biologically active murine interleukin-2 in response to xylan*, May 5, 2005, pp. 1191-1997, vol. 98, Journal of Applied Microbiology.
International Search Report-International Application No. PCT/GB2006/000222.

*Primary Examiner* — Hope Robinson
(74) *Attorney, Agent, or Firm* — Myers Bigel Sibley & Sajovec, PA

(57) ABSTRACT

The invention provides gut commensal bacteria that have been modified to express one or more biologically active polypeptides or protiens, the bacteria includes a promoter, such as a xylanase promoter, which is induced in response to the presence of xylan in the diet and which regulates the expression of the biologically active polypeptide or protien.

12 Claims, 5 Drawing Sheets

GUT COMMENSAL BACTERIUM AND METHODS OF USING THE SAME

RELATED APPLICATIONS

The present application is a 35 U.S.C. §371 national phase application of PCT International Application No. PCT/GB2006/000222, having an international filing date of Jan. 24, 2006 and claiming priority to Great Britain Patent Application No. 0501540.9, filed Jan. 25, 2005, the disclosures of which are incorporated herein by reference in their entireties. The above PCT International Application was published in the English language and has International Publication No. WO 2006/079790.

The present invention relates to the production and secretion of biologically active polypeptide(s) or protein(s) by gut microflora, methods of delivering same and methods of controlling the production and secretion of said biologically active polypeptide(s) or protein(s). The present invention is of particular use in the development of new immunotherapies and especially for the treatment of inflammatory gut diseases.

BACKGROUND

The microbial community in the human large intestine consists of a diverse range of bacteria that are predominantly obligate anaerobes. These bacteria act together to degrade dietary substrates that reach the colon (including insulin, fructo-oligosaccharides and resistant starch), producing a range of products that are important for human health and disease.

The mucosal immune response can be influenced by manipulation of the normal resident bacterial flora. This flora possesses a large variety of biological and immunomodulatory properties that can, directly or indirectly, influence the development and function of the mucosal immune system. Chronic disorders of the gut, for example inflammatory bowel disease (IBD) which includes the disorders Crohn's disease and ulcerative colitis, affect a significant proportion of the population in developed countries. Animal models of mucosal inflammation have been used to try and determine the immune mechanisms involved in the pathogenesis of these diseases. Chronic colitis develops spontaneously in interleukin (IL) $2^{-/-}$ and IL$10^{-/-}$ mice both of which are used as models of IBD. Many other mouse models of IBD have also been described, most of which have targeted deletions of immune response genes. Current treatment of IBD is restricted to anti-inflammatory and immunosuppressive drug therapies including recombinant IL10 and antibodies to tumour necrosis factor-$\alpha$ (TNF-$\alpha$). However, these therapies are not curative and may cause adverse side effects such as toxicity and immunosuppression. Therefore, there is a need for a more targeted and controlled form of immunotherapy.

It is known from the prior art to use commensal, or bacteria that occur naturally in the alimentary canal, such as *Lactobacillus spp.* and *Streptococcus spp.* to treat intestinal inflammation and certain forms of IBD in humans (Shanahan 2001), however these results have limited evidence of success and inconsistent efficacy. It is also known from the prior art to use genetically engineered food grade *Lactococcus lactis* to secrete interleukin-10 (IL10), which when administered intragastrically to two murine models of IBD was shown to be as effective in both preventing and treating disease as the more conventional steroid therapy (Steidler et al. 2000). This *Lactococcus* system has also been used to produce biologically active IL2 and IL6 (Steidler et al. 1995; Steidler et al. 1998). However, a major disadvantage associated with these prior art systems is that *L. lactis* is not able to colonise the gut due to the inability of the organism to bind to the gut epithelium and/or its nutritional dependence on the provision of amino acids and peptides which are unavailable in vivo. Accordingly any in vivo treatment or therapy would require repeated dosing to the appropriate site with the modified organism.

Another biosafety concern and disadvantage of the use of this particular aerobic bacterium is that it could survive outside of the host/patient for sufficient time to be transmitted to others.

A yet further disadvantage of the prior art systems is that there is no means of controlling the constitutive expression of the immunologically active interleukin molecules and these active molecules themselves when overproduced, can have adverse effects. Accordingly the prior art genetically modified probiotic systems lack control and regulation of the activity of probiotic bacteria after administration. This represents a serious safety issue for human therapy.

To address the deficiencies in the prior art and to further develop commensal bacteria as novel delivery systems for biologically active molecules, we have developed genetically engineered probiotic organisms in which the production of immunotherapeutic agents by commensal bacteria in situ can be regulated and controlled by dietary factors.

It is an object of the present invention to engineer a gut commensal bacterium so as to produce and secrete biologically active polypeptide(s) or protein(s) in a regulated manner as a basis for novel immunotherapies for chronic gut disorders.

BRIEF SUMMARY OF THE DISCLOSURE

According to a first aspect of the invention there is provided a gut commensal bacterium deposited under the provisions of the Budapest Treaty at the National Collection of Industrial, Food and Marine Bacteria (NCIMB) Ferguson Building, Craibstone Estate, Bucksburn, Aberdeen, Scotland AB21 9YA on Nov. 29, 2007 and assigned Accession No. 41521 (*Bacteriodes ovatus* BO-KGF), 41522 (*Bacteriodes ovatus* BO-TGF) or 41523 (*Bacteriodes ovatus* BO-MUIL2-S) modified to express one or more biologically active polypeptides or proteins, the bacterium further comprising a promoter which is induced in response to the presence of a dietary factor and which regulates the expression of said biologically active polypeptide or protein.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An operon may be defined as a functional unit consisting of a promoter, an operator and a number of structural genes. An example is the xylanase operon. The structural genes commonly code for several functionally related enzymes, and although they are transcribed as one (polycistronic) mRNA, each has its separate translation initiation site. In the typical operon, the operator region acts as a controlling element in switching on or off the synthesis of mRNA. The xylanase operon is activated in the presence of xylan.

Preferably, the promoter is constitutive and more preferably is the xylanase promoter. Thus it will be appreciated that the expression of the one or more biologically active polypeptides or protiens is controlled by the presence of xylan in the diet. The bacteria can therefore be said to comprise a xylan-inducible regulatory element.

Xylan is a water-soluble, gummy polysaccharide found in plant cell walls and yielding xylose upon hydrolysis. It is therefore a common dietary factor or component, accordingly the inclusion or exclusion of xylan in the diet controls the expression of the biologically active polypeptide or protien. The modified bacteria of the present invention therefore advantageously provide an easily controllable expression system avoiding repeated invasive dosing of an individual since the modified bacteria of the present invention are also able to colonise the gut whilst concomitantly minimising any adverse side-effects.

Preferably, the bacterium is obligate anaerobe and more preferably still said bacterium is either *Bacteroides ovatus* or *Prevotella*.

Preferably, the bacterium in non-pathogenic to man.

"Biologically active" refers to the ability to perform a biological function. The biologically active polypeptide or protein used in the present invention can be either homologous to the bacterium or heterologous thereto, derived from either eukaryotic or prokaryotic or viral sources.

Specific examples of such polypeptides and proteins used in the present invention preferably include insulin, growth hormone, prolactin, calcitonin, luteinising hormone, parathyroid hormone, somatostatin, thyroid stimulating hormone, vasoactive intestinal polypeptide, trefoil factors, cell and tissue repair factors, transforming growth factor β, keratinocyte growth factor, a structural group 1 cytokine adopting an anti-parallel 4α helical bundle structure such as IL-2, IL-3, IL-4, IL-5, IL-6, IL-7, IL-9, IL-10, IL-11, IL-12, IL-13, GM-CSF, M-CSF, SCF, IFN-γ, EPO, G-CSF, LIF, OSM, CNTF, GH, PRL or IFNα/β, a structural group 2 cytokine which are often cell-surface associated, form symmetric homotrimers and the subunits take up the conformation of β-jelly roll described for certain viral coat proteins such as the TNF family of cytokines, eg TNFα, TNFβ, CD40, CD27 or FAS ligands, the IL-1 family of cytokines, the fibroblast growth factor family, the platelet derived growth factors, transforming growth factor p and nerve growth factors, a structural group 3 cytokine comprising short chain α/β molecules, which are produced as large transmembrane pre-cursor molecules which each contain at least one EGF domain in the extracellular region, eg the epidermal growth factor family of cytokines, the chemokines characterised by their possession of amino acid sequences grouped around conserved cysteine residues (the C-C or C-X-C chemokine subgroups) or the insulin related cytokines, a structural group 4 cytokine which exhibit mosaic structures such as the heregulins or neuregulins composed of different domains, eg EGF, immunoglobulin-like and kringle domains.

Alternatively, the biologically active polypeptide can be a receptor or antagonist for biologically active polypeptides as defined above.

The bacterium expresses the biologically active polypeptide or protein and the antigen from nucleic acid contained within it. The nucleic acid may comprise one or more nucleic acid constructs in which nucleic acid encoding the biologically active polypeptide and nucleic acid encoding the antigen are under control of appropriate regulatory sequences for expression in the bacterium.

The bacterium may also express the biologically active polypeptide or protein as a vaccine.

Preferably, the bacterium of the present invention may be modified to express a plurality of biologically active polypeptides or proteins.

According to a further aspect of the invention there is provided a pharmaceutical comprising a gut commensal bacterium modified to express one or more biologically active polypeptides or protiens, the bacterium further comprising a promoter which is induced in response to the presence of a dietry factor and which regulates the expression of said biologically active polypeptide or protien.

Preferably, the pharmaceutical is provided as a composition in a physiologically acceptable carrier, diluent or excipient.

Preferably, the pharmaceutical comprises any one or more of the features hereinbefore recited.

According to a further aspect of the invention there is provided use of a gut commensal bacterium modified to express one or more biologically active polypeptides or protiens, the bacterium further comprising a promoter which is induced in response to the presence of a dietry factor and which regulates the expression of said biologically active polypeptide or protien, in the manufacture of a medicament for the treatment of chronic infammatory bowel disease.

Preferably, the use further comprises any one or more of the features hereinbefore recited.

According to a further aspect of the invention there is provided a method of delivering one or more biologically active polypeptides or proteins or antigens or enzymes or vaccine which comprises administering to a subject a gut commensal bacterium which expresses one or more of said biologically active agents expression of which is under control of a promoter which is activated in the presence of a dietry factor.

Preferably, bacterium expresses more than one biologically active polypeptide or protein or antigen or enzyme or vaccine or a combination thereof.

Preferably, the method comprises the administration of a mixture of bacteria expressing a variety of biologically active polypeptides or proteins or antigens or enzymes or vaccines or a combination thereof.

Thus it will be appreciated that in this embodiment of the invention there is provided, for example and without limitation, bacteria capable of expressing IL2 and bacteria capable of expressing IL12 and/or IL9 and optionally bacteria capable of expressing a cell and tissue repair factor.

Preferably, the method includes any one or more of the features herein before described.

*Bacteroides ovatus*, is a major commensal colonic Gram-negative bacterium in humans and rodents for which cloning systems are available that allow the introduction of foreign DNA into the organism and integration into the genome (Tancula et al. 1992). This organism is also one of only a few that are able to degrade the polysaccharide xylan. We provide evidence for the successful engineering of *B. ovatus* to produce murine IL2 (MuIL2) intracellularly under the control of the xylanase promotor which is active in the presence of xylan. Our results demonstrate that *B. ovatus* can be induced to produce biologically active MuIL2 in response to xylan. We have also engineered a second strain to secrete MuIL2 by adding the *B. fragilis* enterotoxin secretion signal sequence to the protein. The recombinant strains produced MuIL2 only in the presence of xylan as determined by enzyme-linked immunosorbent assay of cell lysates and culture supernatants. The IL2-dependent cell line CTLL-2 was used to demonstrate that MuIL2 produced by both *B. ovatus* strains was biologically active. Moreover, this activity could be blocked by an anti-IL2 neutralising antibody.

According to a further aspect of the invention there is provided a method of treating chronic inflammation of the gut comprising administering to an individual suffering from such a condition a pharmaceutically effective amount of a gut commensal bacterium modified to express one or more biologically active polypeptides or protiens, the bacterium further comprising a promoter which is induced in response to the presence of a dietry factor and which regulates the expression of said biologically active polypeptide or protien.

The use of bacteria of the invention as drug delivery vehicles offers a means of delivering immunomodulatory factors, such as cytokines, and other biologically active molecules directly to the site action to treat chronic inflammation of the gut.

The advantages of this unique form of therapeutic delivery is that it is a convenient and simple means of delivering biologically active proteins directly to their site of action, avoiding the inconvenience and systemic exposure associated with parenteral therapy The present invention will be described by way of example only with brief reference only to the following Figures wherein:

DETAILED DESCRIPTION

Figure 1:
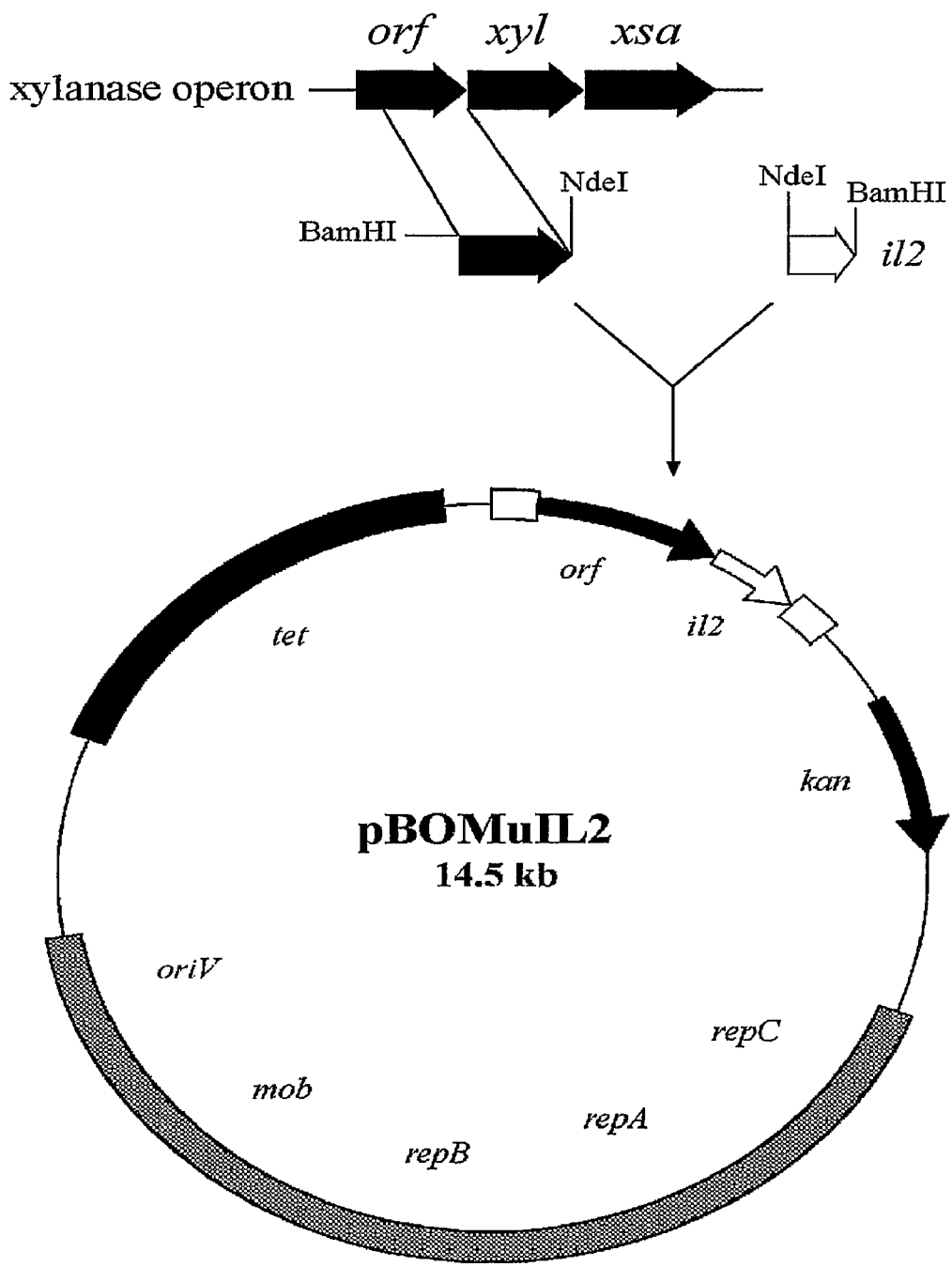
FIG. 1 shows a schematic construction of plasmid pBO-MuIL2.

Bacterial Strains, Plasmids and General DNA Manipulations

*E coli* DH5α and J53/R751 were grown in LB medium. Cultures of *E. coi* J53/R751 were supplemented with 200 μg trimethoprim ml$^{-1}$. *B. ovatus* V975 was grown anaerobically at 37° C. in brain heart infusion (BHI) broth supplemented with 10 μg haemin ml$^{-1}$ or in routine growth medium (RGM) prepared as described by Hespell et al. (1987) and supplemented with 0.1% (w/v) glucose. Where xylan was required, a hot water-soluble fraction of oatspelt xylan was prepared by the method of Hespell and O'Bryan (1992) and added to media at a concentration of 0.2% (w/v). Transfer of plasmids to *B. ovatus* from *E. coli* J53/R751 was carried out by conjugation as described by Valentine et al. (1992). pBT2 (Tancula et al. 1992) was selected in *E. coli* using 50 μg kanamycin ml$^{-1}$. *B. ovatus* transconjugants were selected on BHI-haemin agar containing 200 μg gentamicin ml$^{-1}$ and 5 μg tetracycline ml$^{-1}$. Transconjugants were subsequently grown in medium containing 1 μg tetracycline ml$^{-1}$. *E. coli* was transformed by the method of Hanahan (1983). General DNA manipulations were carried out as described by Sambrook et al. (1990).

Construction of MuIL2-producing and control *B. ovatus* strains

MuIL2-producing strain BOMuIL2. The MuIL2 gene was PCR-amplified from cDNA cloned in pUC13 using primers MuIL2F1 (GCGCATATGGCACCCACTTC MGCTCCAC; SEQ ID NO:1 Ndel site in bold) and MuIL2R1 (GCGG-GATCCTT ATTGAGGGCTTGTTGAGATGATG; SEQ ID NO:2 BamH1 site in bold). A portion of the *B. ovatus* xylanase operon encompassing the 3' half of the orf gene and region between this gene and the xyl gene was amplified from plasmid pOX1 (Whitehead and Hespell 1990) using primers ORFF1 (GCGGGATCCATGGAGCA TGAATGCGTCA; SEQ ID NO:3 BamHI site in bold) and ORFR1 (CATAT-GTTA TATTTTTGAGTMTAAACATTCTAC; SEQ ID NO:4 Ndel site in bold). The MuIL2 and ORF PCR products were cloned into pGEM-T (Promega) to create plasmids pGEM-MuIL2 and pGEM-ORF respectively. MuIL2 was removed from pGEM-MuIL2 with Ndel and ligated into Ndel-digested PGEM-ORF to create pORF-MuIL2. The insert was sequenced to verify the construct. The ORF-MuIL2 construct was removed from pORF-MuIL2 by BamHI digestion and cloned into the BamHI site of pBT2 to create pBOMuIL2. This plasmid was transferred into *B. ovatus* by conjugation and integration of the plasmid into the genome of transconjugants was confirmed by PCR. MUIL2-secreting strain BOMuIL2-S. *B. ovatus* strain BOMuIL2-S was constructed in the same way as strain BOMuIL2 except that the MuIL2 gene was PCR-amplified using primers BFTSIGIL2F (GACATATGMGAATGTAAAGTTACTTT-TAA TGCTAGGAACCGCGGCATTATTAGCTG-CAGCACCCACTTCAAGCTCCAC; SEQ ID NO:5 signal sequence coding region is underlined, Ndel site in bold) and MuIL2R1. This led to the creation of plasmids pGEM-MuIL2-S, pORF-MuIL2-S and pBOMuIL2-S.

Control strain BT2. The control strain containing pBT2 without the MuIL2 gene was constructed as follows. The same portion of the off gene as used above was PCR amplified with primers ORFF1 and ORFR2 (GGATCCT-TATATTTTTGAGTAAT AAACATTCTAC; SEQ ID NO:6 BamHI site in bold) and cloned into pGEM-T to create pGEM-ORFB. The insert was removed with BamHI and cloned into the BamHI site of pBT2 to create pBT-ORF. This plasmid was transferred into *B. ovatus* as described above.

Preparation of Samples of *B. ovatus* producing MuIL2.

*B. ovatus* strains V975, BT2, BOMuIL2 and BOMuIL2-S were grown in 10 ml RGM with or without xylan for 24 h. Strains BOMuIL2 and BOMuIL2-S were also grown for 16 h without xylan and then with xylan for a further 8 h. Following incubation, cells were harvested (5000 g, 30 min, 4° C.). Supernatants were removed and frozen. Cells were washed once in 10 ml RGM and resuspended in 5 ml distilled water. Cells were disrupted by sonication on ice for 4×20 sec at 12 μm (Soniprep 150, MSE). Unbroken cells and cell debris were removed by centrifugation (13,000 g, 20 min, 4° C.). Lysates and supernatants were lyophilized and resuspended in 0.5 ml distilled water.

Assays for Detection of MuIL2

An ELISA incorporating native rat anti-mouse IL2 (clone JES6-1A12) and biotinylated rat anti-mouse IL2 (clone JES65H4) as capture and detection antibodies respectively, was used to quantify levels of MuIL2 produced by recombinant strains of *B. ovatus* and was carried out according to manufacturer's instructions (BD Pharmingen). Recombinant MuIL2 (rMuIL2; Sigma) was used as a control to obtain a standard curve. An IL2 bioassay using the indicator cell line CTLL-2 (Gillis et al. 1978) was used to detect the presence of biologically active MuIL2 in samples (Wadhwa et al. 2000). Briefly, cells were incubated with dilutions of test samples or control rMuIL2 in 96-well plates in duplicate for 18 h. Cells were then pulsed with 0.5 µCi [$^3$H]thymidine, harvested after 4 h and the radioactivity incorporated into DNA estimated by scintillation counting. The assay was also performed in the presence of an IL2 neutralising antibody (clone JES6-1A12). This was added to samples at a concentration of 5 µg ml$^{-1}$ 1 h before addition of cells.

Detection of MuIL2 transcription by RT-PCR

*B. ovatus* V975, BT2, BOMuIL2 and BOMuIL2-S were grown in RGM without xylan for 16 h. A preinduction sample was taken from cultures of BOMuIL2 and BOMuIL2-S before xylan was added to induce transcription of the xylanase operon. Samples were taken from all four cultures after 1 h. Total RNA was extracted from cell samples using the RNeasy kit (Qiagen) followed by treatment with TURBO DNA-free™ (Ambion) to remove any residual contaminating DNA. RT-PCR was performed using the AccessQuick™ RT-PCR System (Promega) and primers for the orf-Muil2 fusion (CCGATGGTACCTGCCATTAAA (SEQ ID NO:7) and CTGTGCTTCCGCTGAGG) SEQ ID NO:8 or the gyrA gene (CTCCATGTCGG TCATCGTTTC (SEQ ID NO:9) and CAAAGGATMCGCATTGCCCA (SEQ ID NO:10)) as a positive control. As a negative control the reaction was performed without the addition of reverse transcriptase.

Construction of *B. ovatus* strains

In order to construct a strain of *B. ovatus* capable of expressing MuIL2 in a xylan-inducible manner, the MuIL2 gene (minus native signal sequence) and 3' portion of the orf gene of the xylanase operon were PCR-amplified and ligated in pGEM-T to give plasmid pORF-MuIL2. An ATG start codon was positioned before the sequence encoding the mature MuIL2 as part of an NdeI site. This ensured translation of the protein. The use of this NdeI site for cloning resulted in a single base change (G to A) in the non-coding region between off and the MuIL2 gene compared to the wild-type region between off and xyl. However, this was not expected to affect MuIL2 expression. The construction of plasmid pBOMuIL2 in FIG. 1 comprises the 3' portion of the *B. ovatus* off gene and entire MuIL2 gene amplified by PCR, ligated together in pBluescript then subcloned into pBT2 to create pBOMuIL2. Only restriction sites used for cloning are shown in the Figure. tet, tetracycline resistance for selection in *B. ovatus*; kan, kanamycin resistance for selection in *E. coli*; oriV, origin of replication; repA, repB, repC encode replication functions and mob is required for mobilization from *E. coli* to *B. ovatus*. The pBOMuIL2 plasmid (FIG. 1) was then successfully transferred to *B. ovatus* V975. The MuIL2-secreting strain, *B. ovatus* BOMuIL2-S, was constructed in the same way except that the forward primer used to PCR-amplify the MuIL2 gene, contained the sequence coding for the *B. fragilis* enterotoxin secretion signal sequence. A control strain, *B. ovatus* BT2 was also constructed by cloning only the off gene into pBT2. Successful construction of the MuIL2 and MuIL2-S expression strains, and BT2 control strain was confirmed by PCR and nucleotide sequencing (data not shown).

EXAMPLE 1

A study was undertaken to assess the ability to colonise the mouse intestine of the genetically engineered strain of *B. ovatus*, *B. ovatus*-MuIL2, designed to produce the murine growth factor Interleukin-2 (IL-2) in the presence of xylan.

Since the utility of using *B.ovatus*-MuIL2 to treat IL2$^{-/-}$ mice is dependent upon demonstrating that it can colonise the mouse colon, we determined if *B.ovatus*-MuIL2 could colonise the colon of wildtype mice. Wildtype, specific pathogen free (SPF), C57BL/6 mice, maintained on a conventional diet (containing xylan), were infected with a single inoculum of ~10$^{10}$ cfu *B.ovatus*-MuIL2 by oral gavage. Colonisation was evaluated 7, 14, 21 and 28 days later by culturing faecal pellets under anaerobic conditions in the presence of antibiotics permissive for the growth of all *Bacteroides* sp., or for the growth of *B.ovatus*-MuIL2 alone. In future experiments the identity of *B.ovatus*-MuIL2 in faecal cultures will be more extensively verified by colony filter hybridisation techniques using a full-length murine IL2 cDNA clone as a probe. As shown in Table 1, *B.ovatus*-MuIL2 was present in faecal pellets of 3/5 animals up to 28 days post inoculation, consistent with their ability to at least transiently colonise the mouse colon. The colons of animals 2, 3 and 5 analysed at 28 days post inoculation contained large numbers (2-8×10$^7$ cfu/g which theoretically could produce 20-80 µg MuIL2) of *B. ovatus*-MuIL2, consistent with faecal bacteria counts. By contrast, the colons of mice No. 1 and 4 contained no *B. ovatus*-MuIL2 consistent with colonisation failure. The efficiency and duration of colonisation could be improved by increasing the number of bacteria in the infective inoculum, or by repeated administration of bacteria.

TABLE 1

Faecal anaerobic bacteria counts from mice "infected" with *B. ovatus*-MuIL2

| Mouse | Total *Bacteroides* (×10$^8$ cfu/g) | | | | | *B. ovatus*-MuIL2 (×10$^4$ cfu/g) | | | | |
|---|---|---|---|---|---|---|---|---|---|---|
| | T0 | T7 | T14 | T21 | T28 | T0 | T7 | T14 | T21 | T28 |
| 1 | 12 | 1.6 | 7.5 | 5.4 | 5.8 | — | nd | nd | nd | nd |
| 2 | 17 | 3.6 | 4.8 | 2.9 | 8.3 | — | 0.67 | 2.74 | 5.4 | 10.1 |
| 3 | 15 | 4.1 | 3.7 | 3.5 | 3.7 | — | 0.53 | 3.2 | 4.9 | 9.3 |
| 4 | 18 | 7.8 | 1.1 | 6.0 | 1.3 | — | nd | nd | nd | nd |
| 5 | 13 | 5.1 | 2.5 | 7.0 | 3.4 | — | 0.21 | 4.61 | 7.9 | 12.2 | nd, Not detectable.

EXAMPLE 2

A study was undertaken to assess the ability of the genetically engineered strain of *B. ovatus*, *B. ovatus*-MuIL2, designed to produce the murine growth factor Interleukin-2 (IL-2) in the presence of xylan to adversely affect the onset or severity of intestinal inflammation that spontaneously occurs in mice genetically deficient of IL-2 (IL-2$^{-/-}$ mice). A concern in using commensal bacteria in immunotherapy protocols for IBD is that the chosen bacteria may, in immunocompromised animals and patients, be "pathogenic" and promote, amplify or sustain intestinal inflammation. Bacteroides, and in particular *B. fragilis* and *B. vulgatis*, have been associated with the development of intestinal inflammation in experimental animal models of IBD and in IBD patients. One study has also identified increased titres of IgA and IgG antibodies reactive with antigens of *B. ovatus* in the sera of IBD patients[5]. However, it is not clear if this was a cause of intestinal inflammation, or was secondary to *Bacteroides* and other commensal bacteria gaining entry to the systemic circulation and triggering immune responses as a result of damage to the epithelial barrier. In view of these findings we thought it necessary to determine if *B. ovatus* has any adverse effect on the development of colitis in IL2$^{-/-}$ mice, which would otherwise confound or counteract any potential benefit that treatment with B.ovatus-MuIL2 might have in these animals.

Two groups (n=6 ea.) of age and sex matched, 3 week old, colitis-free SPF IL2$^{-/-}$ mice maintained on a conventional diet were infected with ~10$^{10}$ cfu B. ovatus (V975) in 200 μl of PBS, or PBS alone every 7 days for 6 weeks by which time untreated IL2$^{-/-}$ mice have developed severe disease. At 3 and 6 weeks post-infection animals were euthanized and tissues (spleen, lymph node and colon) analysed grossly and histologically for disease pathology. A validated histologic inflammatory score was used for blinded evaluation of intestinal inflammation.

Our findings indicate that B. ovatus neither accelerates the onset nor increases the severity of colitis that normally develops in IL2$^{-/-}$ mice. This gross and histological evaluation does not, however, exclude the possibility of there being other, more subtle, changes in for example, the number, distribution and/or activity of immune cells in the tissues and colon of animals treated with B. ovatus. More detailed immunological analyses will therefore, be carried out.

EXAMPLE 3

Figure 2:
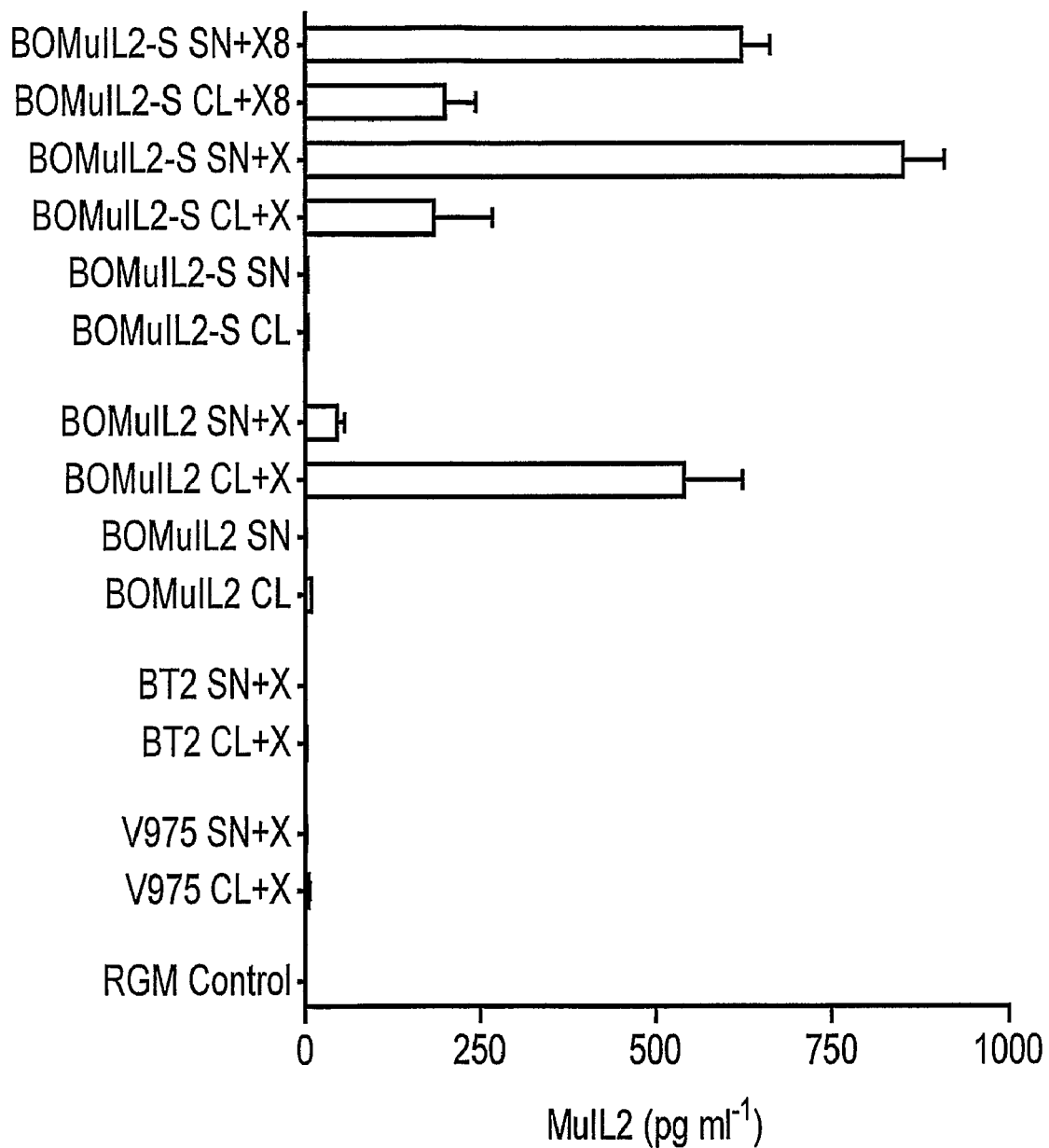
FIG. 2 shows a bar chart of levels of MuIL2 in cell lysates (CL) and culture supernatants (SN) of *B. ovatus* BOMuIL2, *B. ovatus* BOMuIL2-S and control strains (V975 and BT2) grown with xylan for 24 h (+X) or without xylan.

To assess the production of MuIL2 by strains BOMuIL2 and BOMuIL2-S, recombinant strains (BOMuIL2, BOMuIL2-S and BT2) and the wild type strain (V975) were grown in medium with or without xylan. In addition, BOMuIL2 and BOMuIL2-S were grown for 16 h without xylan (RGM with glucose) followed by a further 8 h with xylan to demonstrate the inducible nature of production. Cell lysates and culture supernatants were assayed for MuIL2 by ELISA and bioassay. Representative results from 3 independent experiments are shown in FIG. 2, levels of MuIL2 in cell lysates (CL) and culture supernatants (SN) of B. ovatus BOMuIL2, B. ovatus BOMuIL2-S and control strains (V975 and BT2) grown with xylan for 24 h (+X) or without xylan. BOMuIL2-S was also grown without xylan for 16 h followed by 8 h with xylan (+X8). Test and control strains of B. ovatus were grown in RGM with or without xylan. Cells were harvested and lysed and the amount of MuIL2 in lysates and culture supernatants determined by ELISA. MuIL2 was quantified by comparison to a dilution series of recombinant MuIL2. Data points are mean +/− standard error. MuIL2 was detected in the cell lysate of B. ovatus BOMuIL2 grown with xylan (539.5 pg ml$^{-1}$) and at a lower concentration (44.2 pg ml$^{-1}$) in culture supernatants. For strain BOMuIL2-S, 19.3 times more MuIL2 (849.9 pg ml$^{-1}$) was detected in the supernatant of the culture grown in the presence of xylan compared to BOMuIL2. A lower concentration of MuIL2 (184.3 pg ml$^{-1}$) was detected in the cell lysate of BOMuIL2-S. MuIL2 was not detected in cell lysates or culture supernatants from the two control strains or from B. ovatus BOMuIL2 or BOMuIL2-S cultured in the absence of xylan.

EXAMPLE 4

Figure 3:
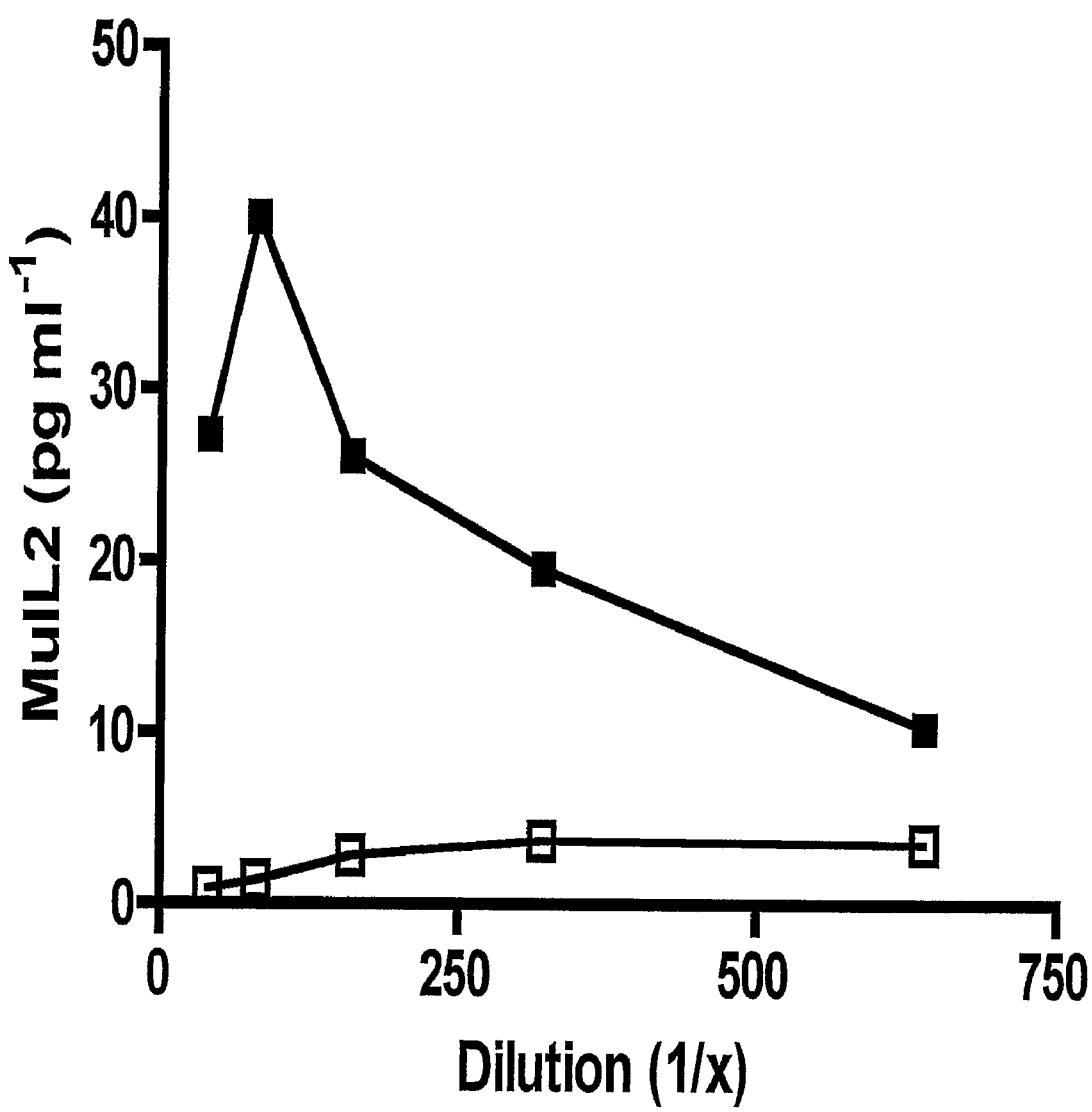
FIG. 3 shows the result of a bioassay of MuIL2 in culture supernatants of *B. ovatus* BOMuIL2-S grown with xylan.

An IL2 bioassay demonstrated that the MuIL2 produced by BOMuIL2-S was biologically active (FIG. 3). FIG. 3 shows the results of a bioassay of MuIL2 in culture supernatants of B. ovatus BOMuIL2-S grown with xylan. Proliferation of CTLL-2 cells was measured by the uptake of [$^3$H]thymidine following incubation with doubling dilutions of:■, B. ovatus BOMuIL2-S supernatant alone; □, B. ovatus BOMuIL2-S supernatant with anti-MuIL2 antibody. MuIL2 was quantified by comparison to a dilution series of recombinant MuIL2. Data points are mean +/− standard error. Biological activity was not detected in supernatants from the control strains or culture medium alone (data not shown). The blocking of proliferation of the indicator cell line by the addition of an anti-MuIL2 antibody demonstrated that the growth promoting activity in culture supernatants of B. ovatus pBO-MuIL2-S was due to MuIL2. In strain BOMuIL2-S, an ATG codon was added to the 5' end of the MuIL2 gene in order to facilitate translation. Consequently, a methionine residue was present on the N-terminus of the mature protein. The results of the bioassay demonstrated that this did not ablate the biological activity of the protein. Likewise, secretion of MuIL2 directed by the B. fragilis enterotoxin secretion signal sequence did not eliminate the biological activity of MuIL2. The higher concentrations of cell lysates and supernatants proved inhibitory to the indicator cell line hence the lower concentration of MuIL2 measured in the ¼₀ dilution of BOMuIL2-S supernatant.

EXAMPLE 5

Figure 4:
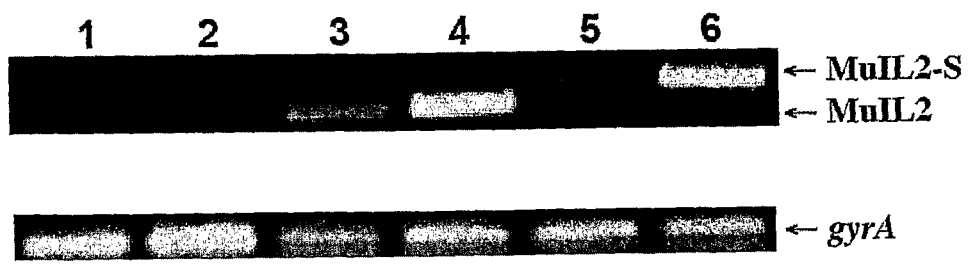
FIG. 4 shows a gel of increased expression of MuIL2 mRNA in response to xylan determined by RT-PCR with test (BOMuIL2 and BOMuIL2-S) or control strains (V975 and BT2) of *B. ovatus* grown for 24 h in RGM without xylan followed by 1 h with xylan.

To confirm transcription of the orf-MuIL2 gene fusion, RT-PCR was performed. B. ovatus BOMuIL2 and BOMuIL2-S were grown in RGM with glucose for 16 h and a cell sample taken. Xylan was then added and samples taken after 1 h. Samples from cultures of control strains were also taken following xylan induction. Total RNA was extracted from cells and RT-PCR performed with primers specific for the orf-MuIL2 construct and for gyrA, a commonly used constitutively expressed control gene. A basal level of transcription could be detected in both BOMuIL2 and BOMuIL2-S strains before addition of xylan that increased 1 h after xylan addition (FIG. 4). FIG. 4 shows increased expression of MuIL2 mRNA in response to xylan as determined by RT-PCR. Test (BOMuIL2 and BOMuIL2-S) or control strains (V975 and BT2) of B. ovatus which were grown for 24 h in RGM without xylan. Xylan was then added and incubation continued for 1 h. Cells were harvested, total RNA extracted and RT-PCR performed to detect MuIL2 and MuIL2-S transcripts. gyrA was used as a positive control. Lanes: 1, V975 grown with xylan for 1 h; 2, BT2 grown with xylan for 1 h; 3, BOMuIL2 grown without xylan; 4, BOMuIL2 grown with xylan for 1 h; 5, BOMuIL2-S grown without xylan; 6, BOMuIL2-S grown with xylan for 1 h.

MuIL2 gene transcription was not detected in the two control strains. Although transcription was detected in the MuIL2-producing strains before the addition of xylan, it was not possible to detect the MuIL2 protein in cell lysates or culture supernatants (FIG. 2).

The data presented herein demonstrates that biologically active MuIL2 can be produced under strict regulation of the xylanase operon in B. ovatus, a member of the resident gut microflora. Furthermore, biologically active MuIL2 could also be secreted by B. ovatus by incorporating the B. fragilis enterotoxin secretion signal sequence. The level of MuIL2 in the culture supernatant of strain BOMuIL2 was relatively low but was increased 19.3 fold by the addition of the secretion signal sequence (strain BOMuIL2-S). The xylanase operon has been advantageously utilised for regulated gene expression by virtue of the inducible nature of this operon in the presence of xylan. Although the promoter of this operon has not been cloned or characterized, the activity of enzymes encoded by genes in the operon have been shown to be upregulated in response to xylan. The system of the present invention also provides for the control or regulation in vivo by dietary intake of xylan. This feature of the invention has the advantage over other inducible systems in that xylan remains undigested as it passes through the gut to the colon and is only degraded in the colon by the action of microbial enzymes.

Although a basal level of transcription was detected in cells grown without xylan, MuIL2 production was at a level too low (<20 pg ml$^{-1}$) for detection by ELISA in cell lysates or culture supernatants. The inability to detect any MuIL2 in xylan-induced cultures of *B. ovatus* pBOMuIL2 following withdrawal of xylan demonstrated the stringency of the xylanase operon and a need for the continued presence of xylan for MuIL2 production (data not shown). The levels of MuIL2 produced and secreted by *B. ovatus* are low, but within physiological range. This is crucial if this system is to be used therapeutically as enough MuIL2 must be produced to have a biological effect but levels must not be so great as to have a detrimental effect. We now intend to test the MuIL2-producing and secreting strains of *B. ovatus* in mouse models of IBD to determine their ability to treat and prevent disease.

EXAMPLE 6

Adult C57BL/6 mice were administered a single dose of recombinant strain of *B. ovatus* expressing the murine IL2 gene by oral gavage ($10^8$ cfu in PBS) and 3 and 7 days (T) later the stools were cultured for the presence of all native *Bacteroides sp.* and the recombinant *B. ovatus* using selective culture conditions and use of antibiotics. Bacteria colonies (cfu) were quantitated after 24 h.

The results show that recombinant *B. ovatus* strain colonises the colon of the majority (4/5) of mice for up to one week after a single dose of bacteria. The presence of the recombinant *B. ovatus* has no discernable impact on the size of the endogenous populations of *Bacteroides*.

TABLE 2

Colonisation of mice by recombinant strains of *B. ovatus*

| Mouse | Total *Bacteroides* cfu g$^{-1}$ | | | Recombinant *B. ovatus* cfu g$^{-1}$ | | |
|---|---|---|---|---|---|---|
| | T0 | T3 | T7 | T0 | T3 | T7 |
| 1 | $1.16 \times 10^9$ | $1.61 \times 10^9$ | $7.54 \times 10^8$ | — | 1208 | 1555 |
| 2 | $1.66 \times 10^9$ | $3.61 \times 10^8$ | $4.75 \times 10^8$ | — | 997 | 1054 |
| 3 | $1.50 \times 10^9$ | $4.06 \times 10^8$ | $3.73 \times 10^8$ | — | 5263 | 5409 |
| 4 | $3.81 \times 10^9$ | $7.77 \times 10^8$ | $1.08 \times 10^9$ | — | 0 | 0 |
| 5 | $1.32 \times 10^9$ | $5.05 \times 10^8$ | $2.50 \times 10^8$ | — | 2105 | 1636 |

EXAMPLE 7

Figure 5:
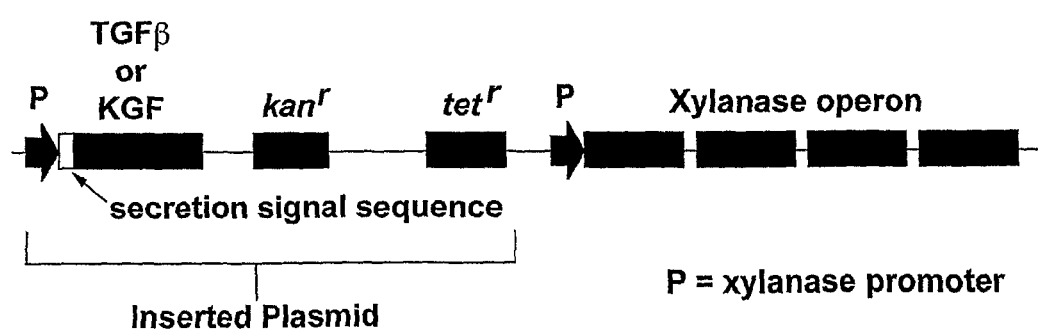
FIG. 5 shows the construct map of *B ovatus* expressing either human TGFβ or KGF.
Figure 6A:
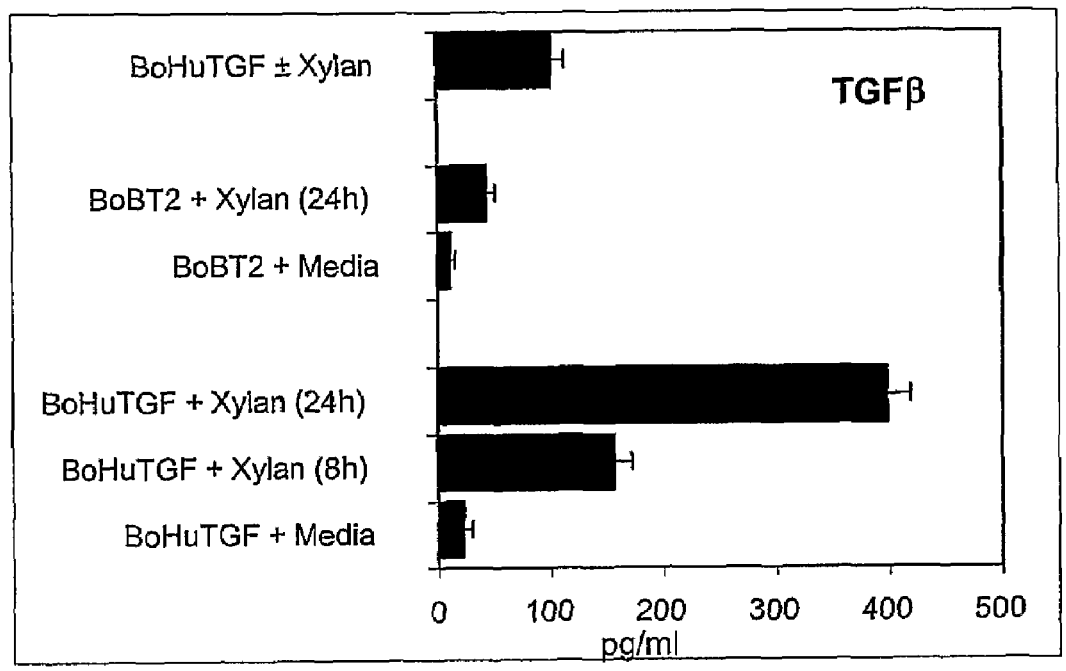
FIG. 6 A shows the production of human cytokines by *B. ovatus* expressing human TGFβ in response to xylan and FIG. 6 B shows the production of human cytokines by *B. ovatus* expressing human KFG in response to xylan.
Figure 6B:
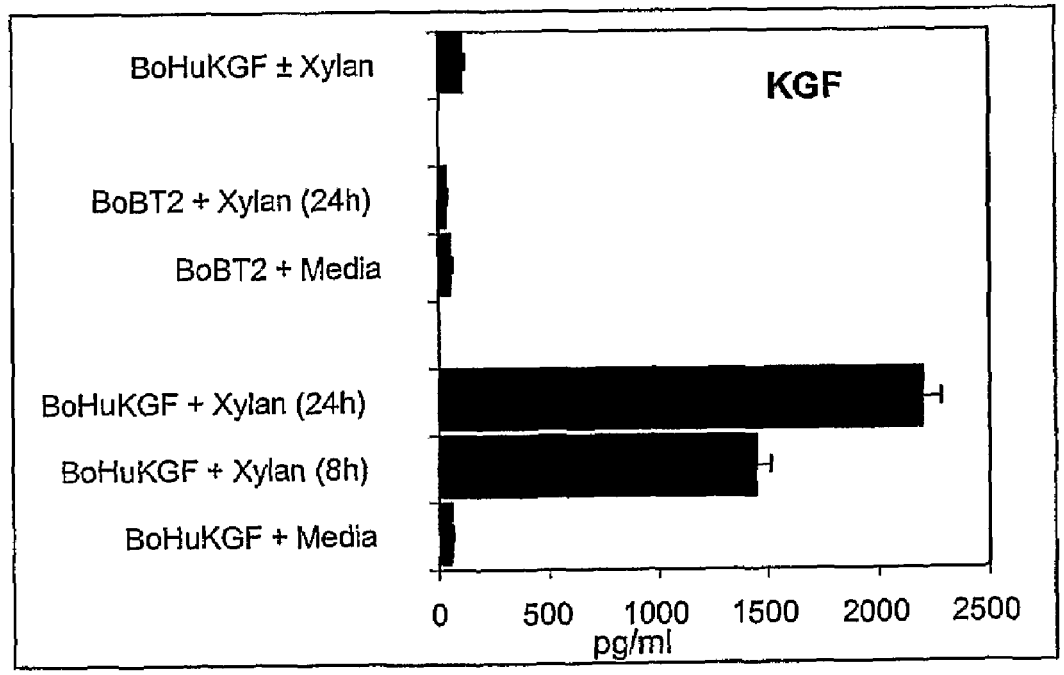

FIG. 5 shows the construct map of *B ovatus* expressing either human TGFβ or KGF. Recombinant strains of *B.ovatus* expressing genes encoding either human KGF (BoHuKGF) or TGFβ (BoHuTGF) or, control strains (BOBTS) that contain no heterologous genes were cultured in complete media alone (Media) or in media containing xylan for 8 or 24 h prior to assaying culture supernatants for TGFβ and KGF by ELISA. Some cultures of recombinant *B.ovatus* were cultured with xylan for 8 h prior to removing media and culturing for a further 24 h in complete media alone (BoHuKGF/TGF±xylan). FIG. 6A shows the graphs of the average amounts (±SEM) of cytokine present in the culture supernatants detected in 3 independent experiments with B.ovatus expressing the gene encoding human KGF TGFβ (BoHuTGF). FIG. 6B shows the same experimental data from *B. ovatus* expressing the gene encoding human KFG (BoHuKGF).

In summary, the ability to engineer commensal bacteria to produce immunomodulatory molecules under the control of dietary factors, as hereinbefore described, offers the potential of providing a more measured, specific arid controlled therapy for chronic gut disorders such as IBD. This approach can be used to deliver a variety of biologically relevant molecules, including cytokines, enzymes and vaccines, with applications in treatment and prevention of a variety of disorders.

REFERENCES

Gillis, S., Ferm, M. M. and Smith, K. A. (1978) T cell growth factor: parameters of production and a quantitative microassay for activity. *Journal of Immunology* 120, 2027-2032.

Hanahan, D. (1983) Studies on transformation of *Escherichia coli* with plasmids. *Journal of Molecular Biology* 166, 557-580.

Hespell, R. B. and O'Bryan, P. J. (1992) Purification and characterization of an α-L-arabinofuranosidase from *Butyrivibrio fibrisolvens* GS113. *Applied and Environmental Microbiology* 58, 1082-1088.

Hespell, R. B., Wolf, R. and Bohast, R. J. (1987) Fermentation of xylans by *Butyrovibrio fibrisolvens* and other ruminal bacteria. *Applied and Environmental Microbiology* 53, 2849-2853.

Saitoh, S., Noda, S., Aiba, Y., Takagi, A., Sakamoto, M., Benno, Y. and Koga, Y (2002) *Bacteroides ovatus* as the predominant commensal intestinal microbe causing a systemic antibody response in inflammatory bowel disease. *Clin. Diagnostic. Lab. Immunol.*, 9, 54.

Sambrook, J., Fritsch, E. F. and Maniatis, T. (1990) *Molecular cloning: a laboratory manual*, Cold Spring Harbor, N.Y.: Cold Spring Harbor Laboratory.

Shanahan, F. (2001) Inflammatory bowel disease: immunodiagnostics, immunotherapeutics, and ecotherapeutics. *Gastroenterology* 120, 622-635.

Steidler, L. (2001) Microbiological and immunological strategies for treatment of inflammatory bowel disease. *Microbes and Infection* 3, 1157-1166.

Steidler, L., Wells, J. M., Raeymaekers, A., Vandekerckhove, J., Fiers, W. and Remaut, E. (1995) Secretion of biologically active murine interleukin-2 by *Lactococcus lactis* subsp. *lactis. Applied and Environmental Microbiology* 61, 1627-1629.

Steidler, L., Robinson, K., Chamberlain, L., Schofield, K. M., Remaut, E., Le Page, R. W. F. & Wells, J. M. (1998) Mucosal delivery of murine interleukin-2 (IL-2) and IL-6 by recombinant strains of *Lactococcus lactis* coexpressing antigen and cytokine. *Infection and Immunity* 66, 3183-3189.

Steidler, L., Hans, W., Schotte, L., Neirynck, S., Obermeier, F., Falk, W., Fiers, W. and Remaut, E. (2000) Treatment of murine colitis by *Lactococcus lactis* secreting interleukin 10. *Science* 289, 1352-1355.

Tancula, E., Feldhaus, M. J., Bedzyk, L. A. and Salyers, A. A. (1992) Location and characterization of genes involved in binding of starch to the surface of *Bacteroides thetaiotaomicron. Journal of Bacteriology* 174, 5609-5616.

Valentine, P. J., Arnold, P. and Salyers, A. A. (1992) Cloning and partial characterization of two chromosomal loci from *Bacteroides ovatus* that contain genes essential for growth on guar gum. *Applied and Environmental Microbiology* 58,1541-1548.

Wadhwa, M., Bird, C., Dilger, P., Mire-Sluis, T. and Thorpe, R. (2000) Quantitative biological assays for individual cytokines. In Cytokine Cell Biology, 3rd edition, ed. Balkwill, F. pp. 207-212. Oxford: Oxford University Press.

Whitehead, T. R. and Hespell, R. B. (1990) The genes for three xylan-degrading activities from *Bacteroides ovatus* are clustered in a 3.8-kilobase region. *Journal of Bacteriology* 172, 2408-2412.

The invention claimed is:

1. A recombinant *Bacteroides ovatus* gut commensal bacterium deposited at the National Collection of Industrial, Food and Marine Bacteria (NCIMB) Accession No. 41521, 41522 or 41523 wherein the bacterium comprises a xylanase promoter that regulates expression of a polypeptide or protein and wherein the promoter is induced in the presence of dietary xylan.

2. The bacterium of claim 1, wherein the bacterium is non-pathogenic to man.

3. The bacterium of claim 1, wherein the polypeptide or protein is selected from the group consisting of insulin, growth hormone, prolactin, calcitonin, luteinizing hormone, parathyroid hormone, somatostatin, thyroid stimulating hormone, vaccines, antigens, vasoactive intestinal polypeptide, trefoil factors, cell and tissue repair factors, transforming growth factor β, keratinocyte growth factor, a structural group 1 cytokine adopting an antiparallel 4α helical bundle selected from the group consisting of IL-2, IL-3, IL-4, IL-5, IL-6, IL-7, IL-9, IL-10, IL-11, IL-12, IL-13, GM-CSF, M-CSF, SCF, IFN-γ, EPO, G-CSF, LIF, OSM, CNTF, GH, PRL or IFNα/β, a structural group 2 cytokine selected from the group consisting of TNFα, TNFβ, CD40, CD27 or FAS ligands, IL-1 family of cytokines, fibroblast growth factor family, platelet derived growth factors, transforming growth factor β and nerve growth factors, a structural group 3 cytokine, epidermal growth factor family of cytokines, chemokines, insulin related cytokines, and a structural group 4 cytokine selected from the group consisting of EGF, immunoglobulin-like and kringle domains.

4. The bacterium of claim 1, wherein the bacterium of NCIMB Accession No. 41521, 41522 or 41523 expresses a plurality of polypeptides or proteins.

5. A pharmaceutical composition comprising:
   (a) a recombinant *Bacteroides ovatus* gut commensal bacterium deposited at the National Collection of Industrial, Food and Marine Bacteria (NCIMB) Accession No. 41521, 41522 or 41523 wherein the bacterium comprises a xylanase promoter that regulates expression of a polypeptide or protein and wherein the promoter is induced in the presence of dietary xylan; and
   (b) a pharmaceutically acceptable carrier, diluent or excipient.

6. A method of treating chronic inflammatory bowel disease comprising administering to a subject in need thereof an effective amount of a recombinant *Bacteroides ovatus* gut commensal bacterium deposited at the National Collection of Industrial, Food and Marine Bacteria (NCIMB) Accession No. 41521, 41522 or 41523 wherein the bacterium comprises a xylanase promoter that regulates expression of a polypeptide or protein and wherein the promoter is induced in the presence of dietary xylan.

7. A method of treating chronic inflammation of the gut comprising administering to a subject in need thereof an effective amount of a recombinant *Bacteroides ovatus* gut commensal bacterium deposited at the National Collection of Industrial, Food and Marine Bacteria (NCIMB) Accession No. 41521, 41522 or 41523 wherein the bacterium comprises a xylanase promoter that regulates expression of a polypetide or protein and wherein the promoter is induced in the presence of dietary xylan.

8. The bacterium of claim 1, wherein polypeptide or protein is obtained from a eukaryotic, prokaryotic or viral source.

9. The recombinant *Bacteroides ovatus* gut commensal bacterium of claim 1, wherein the bacterium further comprises a *Bacteroides fragilis* endotoxin secretion signal sequence to mediate secretion of the Polypeptide or protein.

10. The pharmaceutical composition of claim 5, wherein the bacterium further comprises a *Bacteroides fragilis* endotoxin secretion signal sequence to mediate secretion of the polypeptide or protein.

11. The method of claim 6, wherein the bacterium further comprises a *Bacteroides fragilis* endotoxin secretion signal sequence to mediate secretion of the polypeptide or protein.

12. The method of claim 7, wherein the bacterium further comprises a *Bacteroides fragilis* endotoxin secretion signal sequence to mediate secretion of the polypeptide or protein.

* * * * *

UNITED STATES PATENT AND TRADEMARK OFFICE
CERTIFICATE OF CORRECTION

PATENT NO.         : 7,988,961 B2
APPLICATION NO.    : 11/814739
DATED              : August 2, 2011
INVENTOR(S)        : Farrar et al.

It is certified that error appears in the above-identified patent and that said Letters Patent is hereby corrected as shown below:

In the Patent:
Column 6, Line 11:  Please correct "(GCGCATATGGCACCCACTTC MGCTCCAC"
                        to read -- (GCGCATATGGCACCCACTTC AAGCTCCAC --

Lines 12-13:  Please correct "(GCGGGATCCTT"
                        to read -- (GCGGGATCCTT --

Line 18:  Please correct "(GCGGGATCCATGGAGCA"
                        to read -- (GCGGGATCCATGGAGCA --

Lines 19-20:  Please correct "(CATATGTTA
                        TATTTTTGAGTMTAAACATTCTAC"
                        to read -- (CATATGTTA
                        TATTTTTGAGTAATAAACATTCTAC --

Lines 35-37:  Please correct "(GACATATGMGAATGTAAAGTTACTTT
                        TAA TGCTAGGAACCGCGGCATTATTAGCTGCAG
                        CACCCACTTCAAGCTCCAC;"
                        to read -- (GACATATGAAGAATGTAAAGTTACTTT
                        TAA TGCTAGGAACCGCGGCATTATTAGCTGCAG
                        CACCCACTTCAAGCTCCAC; --

Line 44:  Please correct "(GGATCCT" to read -- (GGATCCT--

In the Claims:
Column 23, Claim 7, Line 4:  Please correct "polypetide" to read -- polypeptide --
        Claim 9, Line 12: Please correct "Polypeptide" to read -- polypeptide --

Signed and Sealed this
Third Day of January, 2012

David J. Kappos
*Director of the United States Patent and Trademark Office*

SEQUENCE LISTING

```
<160> NUMBER OF SEQ ID NOS: 11

<210> SEQ ID NO 1
<211> LENGTH: 29
<212> TYPE: DNA
<213> ORGANISM: Artificial
<220> FEATURE:
<223> OTHER INFORMATION: Oligonucleotide primer sequence

<400> SEQUENCE: 1
gcgcatatgg cacccacttc aagctccac                                29

<210> SEQ ID NO 2
<211> LENGTH: 34
<212> TYPE: DNA
<213> ORGANISM: Artificial
<220> FEATURE:
<223> OTHER INFORMATION: Oligonucleotide primer sequence

<400> SEQUENCE: 2
gcgggatcct tattgagggc ttgttgagat gatg                          34

<210> SEQ ID NO 3
<211> LENGTH: 28
<212> TYPE: DNA
<213> ORGANISM: Artificial
<220> FEATURE:
<223> OTHER INFORMATION: Oligonucleotide primer sequence

<400> SEQUENCE: 3
gcgggatcca tggagcatga atgcgtca                                 28

<210> SEQ ID NO 4
<211> LENGTH: 34
<212> TYPE: DNA
<213> ORGANISM: Artificial
<220> FEATURE:
<223> OTHER INFORMATION: Oligonucleotide primer sequence

<400> SEQUENCE: 4
catatgttat atttttgagt aataaacatt ctac                          34

<210> SEQ ID NO 5
<211> LENGTH: 79
<212> TYPE: DNA
<213> ORGANISM: Artificial
<220> FEATURE:
<223> OTHER INFORMATION: Oligonucleotide primer sequence

<400> SEQUENCE: 5
gacatatgaa gaatgtaaag ttacttttaa tgctaggaac cgcggcatta ttagctgcag    60
cacccacttc aagctccac                                                79

<210> SEQ ID NO 6
<211> LENGTH: 34
<212> TYPE: DNA
<213> ORGANISM: Artificial
<220> FEATURE:
<223> OTHER INFORMATION: Oligonucleotide primer sequence
```

```
<400> SEQUENCE: 6
ggatccttat atttttgagt aataaacatt ctac                                    34

<210> SEQ ID NO 7
<211> LENGTH: 21
<212> TYPE: DNA
<213> ORGANISM: Artificial
<220> FEATURE:
<223> OTHER INFORMATION: Oligonucleotide primer sequence

<400> SEQUENCE: 7
ccgatggtac ctgccattaa a                                                  21

<210> SEQ ID NO 8
<211> LENGTH: 17
<212> TYPE: DNA
<213> ORGANISM: Artificial
<220> FEATURE:
<223> OTHER INFORMATION: Oligonucleotide primer sequence

<400> SEQUENCE: 8
ctgtgcttcc gctgagg                                                       17

<210> SEQ ID NO 9
<211> LENGTH: 21
<212> TYPE: DNA
<213> ORGANISM: Artificial
<220> FEATURE:
<223> OTHER INFORMATION: Oligonucleotide primer sequence

<400> SEQUENCE: 9
ctccatgtcg gtcatcgttt c                                                  21

<210> SEQ ID NO 10
<211> LENGTH: 21
<212> TYPE: DNA
<213> ORGANISM: Artificial
<220> FEATURE:
<223> OTHER INFORMATION: Oligonucleotide primer sequence

<400> SEQUENCE: 10
caaaggataa cgcattgccc a                                                  21

<210> SEQ ID NO 11
<211> LENGTH: 6712
<212> TYPE: DNA
<213> ORGANISM: Bacteroides ovatus

<400> SEQUENCE: 11
aagctttcaa acttgcccgt cagtatggaa atccggatga taaactattc atcaatgatt        60
ataatctgga atataacctc aataagtgtg acggtctgat taaatatgtg gaatacatcg       120
aaagcaaagg ggccacagtg gatggtattg gtacacaaat gcatattgct attgattcca       180
ataaagacaa tattgctcaa atgttccaga aactgggtgc taccggcaag ttgattaaag       240
tatccgagtt ggatattaag gttaacactt cgtcgcctac tactgaaaat ctggcacaac       300
aggcagaaat gtatcagtat gtcattgata tgtacaagaa gtatatccca gcggacaaac       360
aatatggtat taccatctgg ggagtatcgg acaatgaaaa agaacatgtg aattggatac       420
cgaatgatgc tccgaacctt tgggatgcta attatgcacg taaacatgct tataagggag       480
tggccgatgg tttggctggt aaagatgtca gcggagactc taccgagat ttggaataaa       540 tgattttata acgattaaag aaggggagag tgagggttac agtagttgtt attatcttgg       600
```

```
agtggatcaa atgaataaca ataactactg taatccgctc gttctaaaac tttcccttc    660 ctcttgttta tcggtggttt cagcttgaat gtaacattgc aacaagtttt tgtaacatac    720
gtaaacgatg atgtaacaag cgagtaatga tttgaatcag aatttctggg taagtgggaa    780
gaaacttcct aagtttgcaa agtggaatcc cgatggattt cttctcttgc taaattatca    840
tgaaataaag acatataaaa gaaagacaga atgaataagt attggtttta aaggtaggg    900 ttagtagttg tgttcctttg cttcgccttg ttgggcggag caaaggttaa acttccgact    960
cttgtttccg acggaatggt acttcagcgt ggggaacctg tcaatatctg gggaacggct   1020
gatcctgatg aaaccgttga tataactttc ctgaaaaaga aatataagac tgttggggat   1080
gtacaaggta actggaaagt gactttgcct atattgaaag ctggcggacc ttatacgatg   1140
gccattaatg atatcgaatt aaaggatatt cttattggcg atgtttgggt atgttcggga   1200
cagtcgaata tggaattgcc tgtttcacgg gttacagatc gttttcgcga tgaaatatct   1260
acggacagta actatccgat ggtacgctat ataaaaacac ctctgctcta aattttcat   1320 gctccgcagg cagatattcc gggaatttcc tggcaagcga tgactcctga aaatgtgatg   1380
cctttctctg ctttggccta tttcttcgct aaagatgtct atcaaaagac aaaggttccg   1440
gtaggaatca taaattccag tgtcggaggt tcaccggtag aagcgtggat cagtgaggga   1500
gggttgaagc ttttccatt ttatttgaat gaaaagcgta tctatgagtc agacgatttg   1560
atggagtcga tgaaaaaaga ggagaggaag aaaagtcatg cctggaatgt ggcgttgttt   1620
cagggagata aagggatgca tgaggctacc ccttggtatg ctgccgatta tgatgatagc   1680
aattggacag aaacagattt gtttacttcc ggctgggcaa caaacggact gaataccgtc   1740
aatggctccc actggttccg taaagacttt caggtgtctg cacaacaggc gggagagaaa   1800
gcgactcttc gtttgggatg catcgtagat gcagattcgg tctatgtaaa tggcacattt   1860
gtggggactg tctcttatca gtatcctccc cgtatctaca ccattcctgc cggattgttg   1920
aaagccggaa aaaatacaat aaccatacgc cttttcagtt atggcggtcg tcctcaattt   1980
gtaaaggaaa agccttataa aatccttttc ggaaaaggtc agccggaaaa aggagaatcg   2040
gagatcaatt tggagggag ttggaaatat catctcggtg ctcctatgcc cgctgctccg   2100
ggacaaacgg cttttcatta taaacccaca ggactgtata tgcaatgat tgctcctttg   2160 ctgaactata cggtatctgg tgttatctgg tatcagggag aatcgaatgt ctcacgcaga   2220
aatgagtata aagacttgtt gacggctatg attagcgatt ggagacaacg atggaataag   2280
tcggatatgc ctttctatat cattgagctg gcggatttcc tttcacccac agataaagga   2340
ggacgcactg cctgggcgga attccggaaa gcgcaggcgg aagtagccga tacaaataaa   2400
aatgttactg tgattaaaaa tagtgattta ggagaatgga atgatattca tccattggat   2460
aaaaagacgc tagggcaacg agtggcagca gctatcttga tagaaatgaa tacgaaaaac   2520
agaaaatgac caatttatct attttatgga gaatacaata aagaccaatg aagcgaaagg   2580
tttctataaa ctctcttggc ttcaacgtat aggattcggt tccggtgatt tggcgcaaaa   2640 ccttattac cagaccgtat gtatgtatct gctgatttt tataccaatg tatatggact   2700
taaaccggaa gtggcagccg tgatgtttct tattgtcagg atagcggatg tcctttggga   2760
tcctctggtg ggtgctttcg tcgataaaca caatcctaaa ctaggtaaat accgttcata   2820
tcttatttgg ggaggaattc cgctgactgg ttttgctatt ctttgttttt ggaacggctt   2880
ttcgggttca ctgttctatg cctatttcac ttacgtggga ttatccatgt gttatacatt   2940
gattaatgtg ccttatggag cactgaatgc gtcacttacc cgcgatacga atgaaatcac   3000
```

```
ggtgttgacg tcagtgcgta tgtttcttgc caatttgggt ggtttggctg tggcatacgg    3060
tattccgata ctggtgaagg tgttgtctcc cgatggtaaa atcaatacta ctgcatctgc    3120
taacgcatgg tttattacga tgactattta tgctgttatc ggattggcgt tattgatgtt    3180
ctgctttaac cagacgaagg agcgtgtggt tatggatcag gaggagacat ctaaagtaaa    3240
agtgtccgac ttgtgggtag aattttgtag aaataaacct ttgcgtattt ggcgttctt     3300
tttcattact gcttttgcaa tgatggcgat tggtaattct gccggttcat attatatgat    3360
ttataatgta cgtgcaccgg agatgttacc ttatttcatg gccttgggct cgatacccgc    3420
attcattttc atgccgatgg tacctgccat taaacgtgcc attggaaaaa agcaaatgtt    3480
ttatgtattc ctttcagtcg ctatattggg tatggcattg ctgtatatta tttctgtggt    3540
tccggtactc aaaacgcaga tatggttggt ctttgtggcg cagttcataa aatcgacggg    3600
agtcattatt gcgacagggt atatgtgggc tttggttccc gaagtaattt cgtatggcga    3660
atatactcat ggtaaacgta tttcgggtat agtcaatgct ttgactggta ttttctataa    3720
agcgggaatg gctcttggag gagttgtacc gggacttgtt atggcttttg tcggattcga    3780
ccagacaaat gaagtgtcac aatcgccttt tgccgaacag ggaatactgt ggctcgtagc    3840
cgttattccg gcgttgttgc ttttggtcgc tatgttcatt atttctaaat atgaattgga    3900
agataatgtg attgacaata taaatgagga gatagaatcg cgctgtaaaa aaggcgaata    3960
gataagatag tagaatgttt attactcaaa aatataacgt atgaaactca aacgaataat    4020
tctgttgtta ttgacagtga tgttttcttt ttcttatgga gaagttttg cgaaagatgg     4080
aagttcgctg aaaaaggctt tgaaaaacaa gttttttgatt ggcgtgtcag tgaacacaca    4140
tcaaagttcc ggtaaggatg tcgcagctgt tgaaattgta aagaagaatt ttaattccat    4200
cgtggcggaa aactgcatga agtcttctgt cattcatccg aaagaaaata agtataattt    4260
tgcgcaggca gatgaatttg tcagtttttgg tgagagcaat caaatggcta tcattggtca    4320
ctgcctgatt tggcattcac aattggctcc ttggttttgc gtagataagg acgggaataa    4380
tgtttctccg gaagtcctga gaaacggat gaaagaccat atcactacca tcgtgaaacg     4440
ctataaaggc cgtatcaaag ctgggatgt agtaaatgaa gcgattgaag ataatggagc    4500
atatcgcaag acaaagtttt atgagattct gggggaagaa tatatcccat ggctttcca    4560
gtatgcacac gaggctgatc cggatgccga actttactac aatgactact caatggccca    4620
accgggcaga agagaagccg tcgtgaaaat ggtgaacgat ttgaaaaaac gtggaatccg    4680
tattgatgcc ataggtatgc aaggacacat cggcatggca tacccgaaaa tcagtgaatt    4740
tgagaagagt atgctggcct ttgccggaac aggagtgaag ataatgataa cagaactgga    4800
tttgacggtg ataccatcac cgaatcccaa tgtaggtgca gaagtttccg cttcctttga    4860
atataagaaa gagatgaatc cttatccgga tggattaccg gaagaggtat cgaaagcatg    4920
gactgaaaga atgaatgact ttttccgtct gttcctgaaa catcataacc ttatcaccag    4980
ggttactctt tggggagtag ccgatcagaa ctcttggcgt aatgactggc cgatgagagg    5040
ccgcacggat tatccgttac ttttgatcg caattatcag ccgaagccgg tagtcggcct     5100
gattatcaaa gaggctgaaa aaacaaaata gtttctaac agaaaaaccg aaaaagcatg    5160
aaaacagaaa aagatatttt agttcccggt gattatatgg ctgaccctgc cgtacatgta    5220
tttgatggca aactgtatat ttatccctcg cacgattggg aaagtggtat tgctgaaaat    5280
gataatggcg atcatttcaa tatgaaagat tatcacgtgt attctatgga tgatgtgatg    5340
aacggtgaaa taaaagatca tggagtggtg ctttccacag aggatattcc ttgggcgggc    5400
```

```
cgtcaactat gggattgtga tgtggtttgt aaagatggta agtactatat gtattttcca    5460
ttgaaagatc agaatgatat atttcgtatc ggggtagctg tgagtgataa accttatggt    5520 cctttatac cggaagctaa tccgatgaaa ggaagttaca gcatcgatcc ggctgtatgg     5580
gatgacggag atggtaacta ttatatatat ttcggtggat tgtggggtgg acaacttcaa    5640
cgttaccgta ataataaagc cttggaatct gccattttgc cggaaggaga ggaggaggca    5700
atcccgtcgc gtgttgctcg tttgagtgaa gacatgatgg agtttgccga agaacccgt     5760 gcagtggtaa ttctggatga agacggtaag ccattgacag caggggatac ggaacgccgt    5820
ttcttcgaag cttcgtggat gcataaatat aatggtaaat actattttc ctattctacg     5880 ggagacactc atttgctctg ctatgcaaca ggtgataacc cttatggtcc gtttacttat    5940
cagggagtca ttctgactcc ggtggtagga tggactactc accatgctat tgtagagttt    6000
aaaggtaagt ggtatctgtt tcatcacgat tgtgtaccat cagagggaaa gacttggctc    6060
cgtagcttga aagtctgtga acttcagtat gatgcagacg ggcgaatcat tactatcgag    6120
ggaaaagatg aataatagga tacattaaaa caaccgcctc tatttgaaaa acatacctac    6180
ttttaccaga atattaggta atagggattt ttcaggtaga ggcggttatt attaactatg    6240
aatgcttaat ttacttatgc tatcatactg taaattaatt gtgataacat actttgtact    6300
atgagaaata tatttgcatt gacattcact ttgttttttt gcttttcttc tatttgggca    6360
gaagatggaa gtgccttgtg gcttcgttat gcatcgggag cgaaagcgga aattaccagc    6420
aagaaacaat cacctacatt acgtattgcg gtttccgaat tacagaactt ctggcaggga    6480
ggaatcccgg ttactttgga ggtccggaac aataaagaac ttcgtgcact tggaaatgag    6540
ggatatacga ttcagacctc caaaggtggc aatcaaataa cgatagcttc ttccggtgaa    6600
caaggagtac tttatggaac gtatcattta ctccgtctgc aagctaccgg acaactaccg    6660
gaatcagctt tgcaatccct caatttctcc gaacgacctg attatcgaat tc            6712
```